US00PP13784P29

(12) United States Plant Patent
Hofmann

(10) Patent No.: US PP13,784 P2
(45) Date of Patent: May 6, 2003

(54) VARIETY OF GERANIUM PLANT NAMED 'PACWEI'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/120,270

(22) Filed: Apr. 10, 2002

(51) Int. Cl.[7] ..... A01H 5/00
(52) U.S. Cl. ..... Plt./326
(58) Field of Search ..... Plt./326

*Primary Examiner*—Kent Bell
(74) *Attorney, Agent, or Firm*—Webb Ziesenhiem Logsdon Orkin & Hanson, P.C.

(57) ABSTRACT

Disclosed is a new and distinct zonal geranium plant named 'Pacwei' having large white colored flowers and dark green foliage.

1 Drawing Sheet

VARIETAL DENOMINATION

'Pacwei'.

BOTANICAL CLASSIFICATION

*Pelargonium×hortorum* (zonal geranium).

BACKGROUND OF THE INVENTION

The present invention comprises a new and distinct cultivar of zonal geranium known by the varietal name 'Pacwei'. The new variety is the result of in vitro mutation breeding in Dresden, Germany of the unpatented variety 'PAC Blanca'. The new variety exhibits dark foliage like its parent, but differs in its flower color shade, flower size and umbel size. The new variety was first asexually reproduced by cuttings in Dresden, Germany in 2000. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via cuttings carried out in Dresden, Germany. Plants described were about 9 months old. The color readings were taken indoors on plants grown in pots in greenhouses during Summer. Color references are primarily to The R.H.S. Colour Chart of The Royal Horticultural Society of London.

PLANT

Form: Upright.
Height from media surface to top of foliage: 27–32 cm.
Height from media surface to top of umbels: 35–43 cm.
Growth: Erect, well branched.
Strength: Does not require artificial support.
Roots: 3.5 weeks to develop.
Time to produce a flowering plant: 3 months.

Leaves: Opposite arrangement; weak zonation.
*Length.*—5 cm.
*Width.*—9 cm.
*Shape.*—Overall: Reniform. Base: Cordate. Apex: Pointed.
*Margin.*—Crenate.
*Texture.*—Hairy.
*Color.*—Upper surface: 137A with zone of 139A. Lower surface: 137B.
Ribs and veins:
*Venation.*—Net-veined.
*Color.*—137C.
Petioles:
*Color.*—137C.
*Length.*—5–6 cm.
Stem/branches:
*Color.*—137C.
*Overall stem length.*—28 cm.
*Internode length.*—2–4 cm.
*Lateral branch length.*—20 cm.

THE BUD

When just beginning to open:
Shape:
*Overall.*—Umbel-shaped.
*Individual bud.*—Shell-shaped.
Color: 158C.
Size:
*Cluster.*—5 cm in diameter.
*Individual bud.*—Length: 1.5 cm. Width: 0.8 cm.

INFLORESCENCE

Flowering: Continuous through Summer until frost.
Borne: Umbel; flower on pedicel, pedicel on peduncle.
Umbel:
*Width.*—10 cm.
*Depth.*—5 cm.
*Number of flowers per umbel.*—20–25.
*Lastingness.*—4–6 weeks.
Flowers:
*Form.*—Zygomorph, semi-double.
*Size.*—Diameter: 4.5–5.0 cm. Depth: 1.5 cm.
*Petals.*—Color: Upper surface: 157D. Lower surface: 157D. Quantity: 8, including petaloids. Size: Length:

3 cm. Width: 2 cm. Shape: Overall: Oval. Apex: Round. Base: Pointed. Margin: Entire. Texture: Smooth.

Petaloids:
*Quantity.*—2–3.
*Shape.*—Irregular.
*Color.*—157D (both surfaces).

Sepals:
*Shape.*—Overall: Narrow, linear. Apex: Pointed. Base: Fused.
*Color.*—Upper Surface: 137D. Lower Surface: 137D.
*Size.*—Length: 1 cm. Width: 0.3 cm.

Pedicel:
*Length.*—3–4 cm.
*Color.*—138B.

Peduncle:
*Length.*—12–14 cm.
*Color.*—138B.

Disease/pest resistance: No susceptibility to diseases or pests noted to date.

REPRODUCTIVE ORGANS

Stamens:
*Anthers.*—2 mm long.
*Filaments.*—Length: 9 mm. Color: 145D.
*Pollen.*—169A.

Pistils:
*Number.*—One, 5–6 parted.
*Length.*—3 mm.
*Stigma.*—157C.
*Style.*—Length: 0.4 mm. Color: 157C.

Ovaries: Superior, hairy.
*Length.*—0.5 cm.
*Color.*—146D.

Fruit: If present, maximum 5 per flower, 0.3–0.5 cm long, 165A.

GENERAL CHARACTERISTICS

1. Vigorous growth.
2. Dark foliage.
3. Compact, good branching.
4. Pure white, large flowers.
5. Heat tolerant.
6. Rich flowering.

I claim:

1. A new and distinct variety of geranium plant substantially as shown and described.

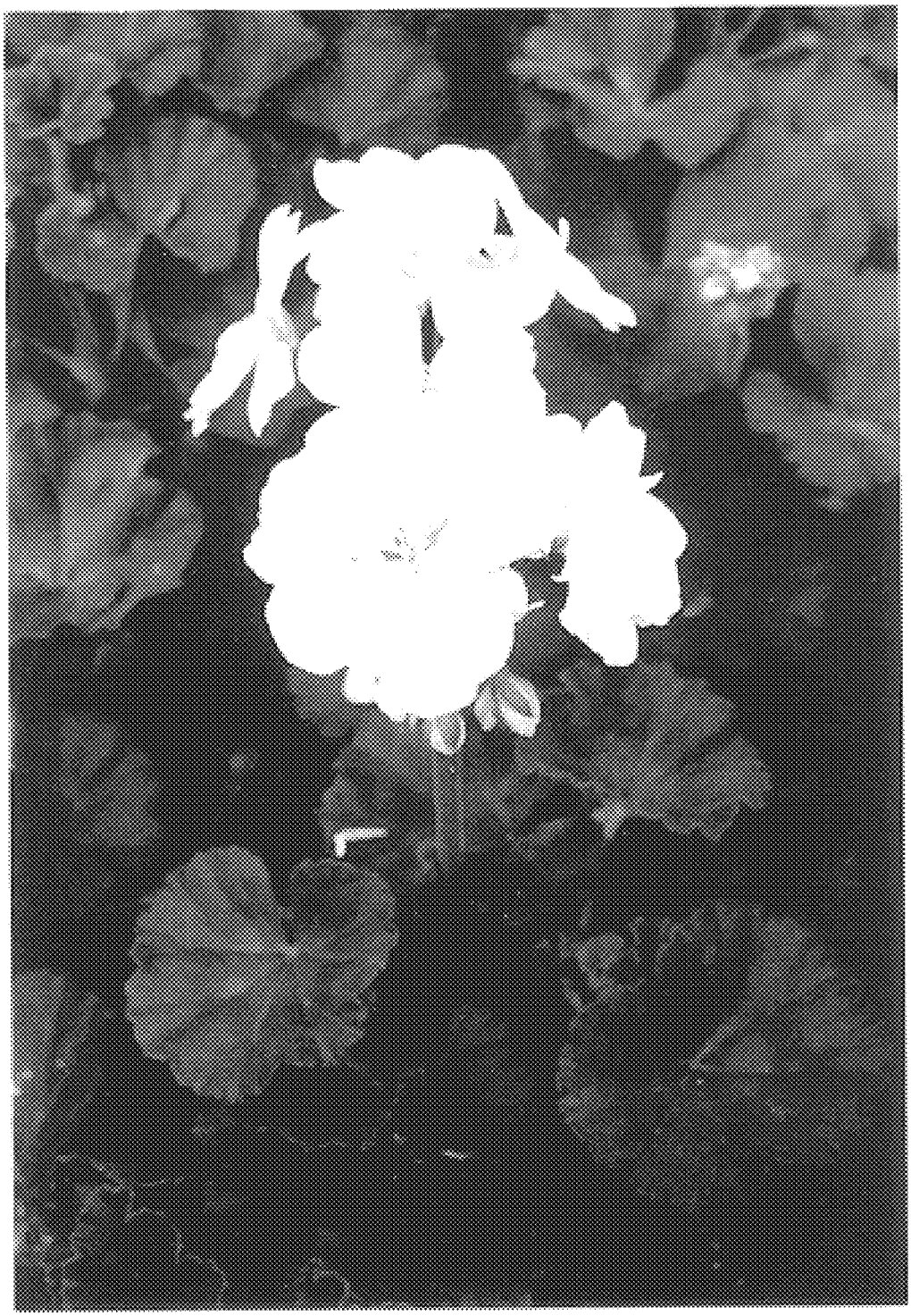

* * * * *